United States Patent [19]

Kuus-Reichel et al.

[11] Patent Number: 5,856,182
[45] Date of Patent: Jan. 5, 1999

[54] MONOCLONAL ANTIBODIES SPECIFIC FOR THE PSA-ACT COMPLEX

[75] Inventors: Kristine Kuus-Reichel, San Diego; Harry Jay Linton, Encinitas; Janice K. Payne, San Diego; Tang J. Wang, Poway, all of Calif.

[73] Assignee: Beckman Coulter, Inc., Fullerton, Calif.

[21] Appl. No.: 749,525

[22] Filed: Nov. 18, 1996

[51] Int. Cl.$^6$ .............................. C12N 5/06; C12N 5/16; G01N 33/574; C07K 16/00
[52] U.S. Cl. .................. 435/330; 530/387.7; 530/388.8; 435/7.23
[58] Field of Search .............................. 424/184.1, 193.1, 424/277.1; 435/7.1, 7.23, 330; 530/387.7, 388.8, 388.85

[56] References Cited

U.S. PATENT DOCUMENTS 5,501,983  3/1996  Lilja et al. .............................. 436/518

FOREIGN PATENT DOCUMENTS

0635575 A1  6/1994  European Pat. Off. .

OTHER PUBLICATIONS

Sandhu, J.S. "Protein Engineering of Antibodies" in Critical Reviews in Biotechnology, vol. 12, issues 5 and 6, pp. 437–445, 1992.

Paul, W. E. "Fundamental Immunology" Second Edition, Raven Press, NY, pp. 177–181, 1989.

Schlom, J. "Monoclonal Antibodies: They're more and less than you think" in Molecular Foundations of Oncology, ed. Samual Broder, pp. 95–134, 1991.

The Establishment and Evaluation of Luminescent–Labelled Immunometric Assays for Prostate–Specific Antigen–$\alpha_1$–Antichymotrypsin Complexes in Serum, W G. Wood, et al., Eur. J. Clin. Chem. Clin. Biochem. vol. 29, pp. 787–794, 1991.

A Complex between Prostate–Specific Antigen and $\alpha_1$–Antichymotrypsin Is the Major Form of Prostate–specific Antigen in Serum of Patients with Prostate Cancer: Assay of the Complex Improves Clinical Sensitivity for Cancer. U. Stenman, et al., Cancer Research 51, 222–226 Jan. 1, 1991.

Serum Prostate Specific Antigen Complexed to $\alpha 1$–Antichymotrypsin As An Indicator Of Prostate Cancer, Anders Christensson, et al., The Journal of Urology, vol. 150, 100–105, Jul. 1993.

Correlation of Serum Concentrations of PSA–ACT Complex With Total PSA in Random and Serial Specimens From Patients With BPH and Prostate Cancer, J. T. Wu, et al. Journal of Clin. Lab. Anal. 9:15–24 (1995).

Enzymatic activity of prostate–specific antigen and its reactions with extracellular serine proteinase inhibitors, A. Christensson, et al., Eur. J. Biochem., 194, 755–763, 1990.

Purification of PSA–ACT Complex: Characterization of PSA–ACT Complex by Various Chromatographic Procedures, Jame T. Wu, et al., Journal of Clin. Lab. Analysis 9:25–31 (1995).

Free, Complexed And Total Serum Prostate Specific Antigen: The Establishment Of Appropriate Reference Ranges For Their Concentrations And Ratios, Joseph E. Oesterling, et al., The Journal of Urology, vol. 154, 1090–1095, Sep., 1995.

Characterization Of Five Different Epitopes Of Anti–PSA Monoclonal Antibodies, Tang J. Wang, et al., Clin. Chem., vol. 41, No. 6, 1995.

Prostate–Specific Antigen in Serum Occurs Predominantly in Complex with $\alpha_1$–Antichymotrypsin, Hans Lilja, et al. Clin. Chem. 37/9, 1618–1625 (1991).

Double–Label Time–Resolved Immunofluorometric Assay of Prostate–Specific Antigen and of Its Complex with $\alpha_1$–Antichymotrypsin, Jari Leinonen, et al., Clin. Chem., Vol. 39, No. 10, 1993.

Improved Separation Between Normals, Benign Prostatic Hyperplasia (BPH), and Carcinoma of the Prostate (CAP) by Measuring Free (F), Complexed (C), and Total Concentrations (T) of Prostate Specific Antigen (PSA), Hans Lilja, et al., Journal of Urology, 151, 400A, 1994.

*Primary Examiner*—Sheela Huff
*Assistant Examiner*—Yvonne Eyler
*Attorney, Agent, or Firm*—William H. May; Margaret A. Kivinski

[57] ABSTRACT

Monoclonal antibodies have been developed which specifically bind the PSA-ACT complex without significant cross-reactivity with PSA, ACT or CG-ACT. The antibodies were generated using a unique immunogen comprising a PSA-ACT complex having bound to monoclonal antibodies against PSA and monoclonal antibodies against ACT. It is theorized that the antibodies against PSA and ACT block immunodominant sites on the PSA-ACT complex. The antibodies generated against the unique immunogen specifically bind the PSA-ACT complex, but have no significant cross-reactivity with either PSA or ACT. The monoclonal antibodies of the present invention can be used in immunoassays to specifically detect PSA-ACT in a sample.

4 Claims, 1 Drawing Sheet

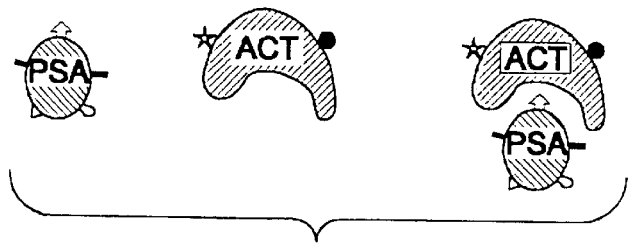
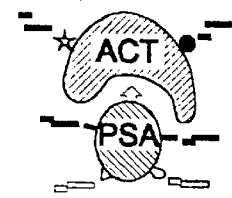
Fig. 1   Fig. 2
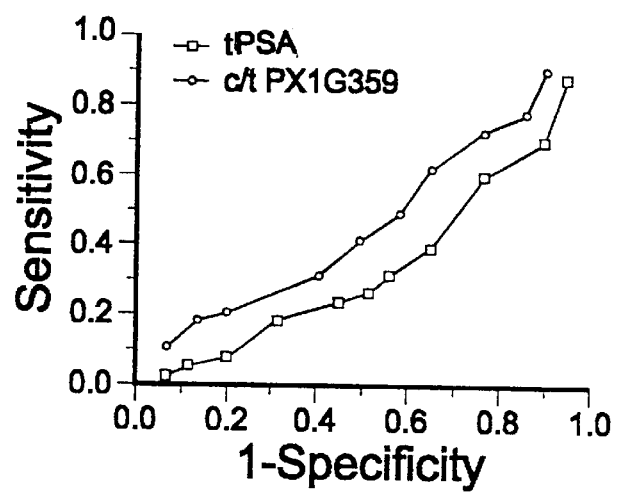
Fig. 3
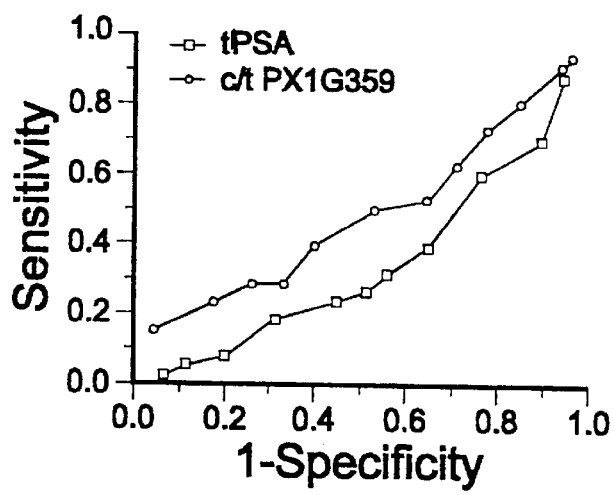
Fig. 4

MONOCLONAL ANTIBODIES SPECIFIC FOR THE PSA-ACT COMPLEX

FIELD OF THE INVENTION

The present invention relates to monoclonal antibodies, in particular, monoclonal antibodies which specifically bind the complex formed between prostate specific antigen (PSA) and the protease inhibitor $\alpha_1$-antichymotrypsin (ACT), the PSA-ACT complex.

BACKGROUND OF THE INVENTION

Prostate specific antigen (PSA) is a 34 kDa secretory protein of the human prostate (Wang, et ale, Invest. Urol., 17:159–163, 1979). The concentration of PSA in prostatic fluid and seminal plasma is very high, ranging from 0.5 to 2 mg/ml (Wang et al., Prostate, 2:89–96, 1981; Lilja et al., Prostate, 12:29–38, 1988). PSA is also present at elevated levels in serum of patients with prostate cancer. Because of this, serum PSA level has become an important tumor marker for the early detection and monitoring of patients with prostate cancer.

Serum PSA level is also elevated in patients with the non-cancerous disease, benign prostatic hyperplasia (BPH). Considerable studies have been performed in an effort to distinguish an elevated PSA serum level that is associated with prostate cancer from one that is associated with BPH. One area of study has focused on the various forms of PSA present in serum.

PSA has been shown to complex with protease inhibitors, such as $\alpha_1$-antichymotrypsin (ACT) and $\alpha_2$-macroglobulin (Christensson, et al., Eur. J. Biochem., 194:755–763, 1990). In serum, the majority of PSA is complexed with protease inhibitors, with only a small percentage of PSA remaining in its free form (Lilja, et ale, Clin. Chem., 37:1618–1625, 1991). Monitoring the relative amounts of the different forms of PSA (complexed versus free) in serum has been shown to be of potential clinical value in differentiating prostate cancer and BPH (Stenman et al., Cancer Res., 51:222–226, 1991; Christensson, et al., J. Urol., 150:100–105, 1993).

One way to detect the presence of PSA in a sample is by immunoassay. Immunoassays are assay systems that exploit the ability of an antibody to specifically recognize and bind to a particular target molecule. The region of a molecule that is recognized by an antibody, and to which the antibody binds is referred to as an "epitope." Large molecules, such as proteins, possess multiple epitopes. The molecule that is recognized by the antibody is also referred to as an "antigen."

Immunoassays are used extensively in modern diagnostics (Fackrell, J. Clin. Immunoassay 8:213–219, 1995). A large number of different immunoassay formats have been described (Yolken, R. H., Rev. Infect. Dis. 4:35, 1985); Ngo, T. T. et al., Enzyme Mediated Immunoassay, Plenum Press, N.Y., 1985). Immunoassay formats have been developed that are amenable to large scale usage.

The simplest immunoassay involves merely incubating an antibody that is capable of binding to a predetermined molecule (i.e. the "analyte") with a sample that is suspected to contain the analyte. The presence of the target molecule is determined by the presence, and is proportional to the concentration, of any immune complexes that form through the binding of antibody and analyte. In order to facilitate the separation of such immune complexes from the unbound antibody initially present, a solid phase is typically employed. In more sophisticated immunoassays, the concentration of the target molecule is determined by binding the antibody to a support, and then incubating the bound antibody in the presence of the analyte-containing sample.

Target molecules that have become bound to the immobilized antibody can be detected in any of a variety of ways. For example, the support can be incubated in the presence of a labeled, second antibody (i.e. a "sandwich" immunoassay) that is capable of binding to a second epitope of the target molecule. Immobilization of the labeled antibody on the support thus required the presence of the target, and is proportional to the concentration of the target in the sample. In an alternative assays, the sample is incubated with a known amount of labeled target and antibody binding site. Any target molecules present in the sample compete with the labeled target molecules for the antibody binding sites. Thus, the amount of labeled target molecules that are able to bind to the antibody is inversely proportional to the concentration of target molecule in the sample.

The various immunoassay formats can be further divided into two main classes, depending upon whether the assay requires the separation of bound species from unbound species. Heterogeneous immunoassays require such purification, and hence entail a separation or isolation step. Because homogeneous assays lack a separation step, and are more easily automated, they may be more desirable than heterogeneous assays in applications that entail the screening of large numbers of patients.

Regardless of immunoassay format, the utility of an immunoassay in detecting an analyte depends upon its capacity to report the extent of the formation of immune complexes between the antibody employed and the analyte whose presence or concentration is being measured. One approach for increasing this capacity involves labeling one or more the reagents.

A wide array of labels (such as radioisotopes, enzymes, fluorescent moieties, chemiluminescent moieties, or macroscopic labels, such as a bead, etc.) have been employed in order to facilitate the detection of immune complexes (Chard, T. et al., Laboratory Techniques and Biochemistry in Molecular Biology, North Holland Publishing Company, N.Y., 1978; Kemeny, D. M. et al., ELISA and Other Solid Phase Immunoassays, John Wiley & Sons, N.Y., 1988).

Immunodetection of the various forms of PSA in serum has become an important objective. Immunoassays to detect PSA in serum have been developed. These assays, however, measure all immunologically detectable forms of PSA in serum, i.e., PSA in its free form, in addition to PSA complexed with ACT. Immunoassays to measure only the free form of PSA have also been developed.

Prior immunoassays, however, have not been capable of selectively detecting the PSA-ACT complex. This is in part because antibodies that are specific for the PSA-ACT complex have not been developed. Because of the importance of detecting PSA, PSA-ACT and the relative amounts of each, it would be desirable to have an immunoassay capable of specifically detecting the PSA-ACT complex.

Previous attempts to generate antibodies specific for the PSA-ACT complex have been unsuccessful. Antibodies to PSA-ACT previously developed are not specific to PSA-ACT, but also bind free PSA, ACT or other serum ACT complexes, such as cathepsin G-ACT (CG-ACT). It is theorized that immunodominant sites on the PSA-ACT complex are not specific for the complex, but are also active for either PSA or ACT. What is needed are antibodies to PSA-ACT that do not significantly cross-react with PSA, ACT or CG-ACT.

SUMMARY OF THE INVENTION

In accordance with an embodiment of the present invention, a panel of monoclonal antibodies have been developed which specifically bind the PSA-ACT complex. The monoclonal antibodies of the present invention do not significantly cross-react with PSA, ACT or CG-ACT.

The present invention is further embodied in a unique immunogen which is useful in generating the monoclonal antibodies which specifically bind PSA-ACT. The immunogen comprises a PSA-ACT complex having at least one monoclonal antibody specific for PSA bound to the PSA-ACT complex, as well as at least one monoclonal antibody specific for ACT bound to the PSA-ACT complex. In a preferred embodiment, four anti-PSA antibodies and two anti-ACT antibodies are bound to the PSA-ACT complex.

A further aspect of the invention is an immunoassay for detecting PSA-ACT in a sample which utilizes the monoclonal antibodies of the present invention which specifically bind the PSA-ACT complex and do not significantly cross-react with PSA, ACT or CG-ACT.

BRIEF DESCRIPTION OF THE FIGURES

FIG. 1 is a schematic representation of PSA, ACT and the PSA-ACT complex.

FIG. 2 is a schematic representation of a unique immunogen in accordance with an embodiment of the present invention.

FIG. 3 is a graphical representation of an ROC analysis for an immunoassay for the PSA-ACT complex using a monoclonal antibody specific for PSA-ACT in accordance with an embodiment of the present invention.

FIG. 4 is a graphical representation of an ROC analysis for an immunoassay for the PSA-ACT complex using another monoclonal antibody specific for PSA-ACT in accordance with an embodiment of the present invention.

DETAILED DESCRIPTION OF THE PREFERRED EMBODIMENTS

In accordance with embodiments of the present invention, there are provided monoclonal antibodies that specifically bind the PSA-ACT complex and which do not significantly cross-react with PSA, ACT or CG-ACT. Among the monoclonal antibodies that have been developed which exhibit these characteristics are PX1G 54, PX1G 283, PX1G 359 and PX1G 460.

Another aspect of the present invention is a unique immunogen capable of producing the monoclonal antibodies described which specifically bind PSA-ACT. The immunogen comprises a PSA-ACT complex and has bound to the complex one or more monoclonal antibodies against PSA and one or more monoclonal antibodies against ACT.

The invention further encompasses hybridoma cell lines capable of producing the antibodies which specifically bind PSA-ACT. Also provided are immunoassays for detecting PSA-ACT in a sample which utilize the monoclonal antibodies obtained in accordance with the present invention.

Without intending to be bound by theory, it is believed that the PSA-ACT complex has multiple immunoreactive binding sites. A schematic representation of the PSA molecule, the ACT molecule, and the PSA-ACT complex is depicted in FIG. 1. PSA may have at least five dominant immunoreactive binding sites, some of which remain active upon the formation of a complex of PSA with ACT. Likewise, ACT may have several dominant immunoreactive binding sites which remain active upon the formation of the PSA-ACT complex. In order to inactivate immunodominant binding sites of PSA and ACT within the PSA-ACT complex, antibodies specific for PSA and ACT are bound to the complex to block the complex non-specific sites. It is believed that the remaining active sites are specific for the PSA-ACT complex.

In accordance with an embodiment of the present invention, at least one antibody against PSA is bound to a PSA-ACT complex. In a preferred embodiment, four anti-PSA antibodies are bound to the PSA-ACT complex. The antibodies can be selected from the group consisting of PSA 399, PSM 773, PSJ 206 and PSM 80.

In accordance with another embodiment of the present invention, at least one antibody against ACT is bound to the PSA-ACT complex. In a preferred embodiment, two anti-ACT antibodies are bound to the PSA-ACT complex. The at least one monoclonal antibody against ACT can be selected from the group consisting of AC1A 212 and AC1A 285.

In a most preferred embodiment, four anti-PSA and two anti-ACT monoclonal antibodies are bound to the PSA-ACT complex. FIG. 2 schematically depicts a unique immunogen in accordance with this embodiment of the invention.

The monoclonal antibodies useful in the present invention can be obtained by a method described by Milstein and Kohler, Nature, 256:495–497, 1975. The details of the process are well known and will not be repeated here. In general, the process involves injecting a mouse with an immunogen. In the present case, the immunogen is a PSA-ACT complex having anti-PSA and anti-ACT antibodies bound thereto. The mouse is subsequently sacrificed and cells taken from its spleen are fused with myeloma cells. The result is a hybrid cell, referred to as a "hybridoma," that reproduces in vitro. The population of hybridomas is screened and otherwise manipulated so as to identify and isolate individual clones each of which secretes a single antibody species to the antigen. Each individual antibody species obtained in this way is the product of a single B cell from the immune animal generated in response to a specific antigenic site recognized on the immunogenic substance.

Upon introduction of an immunogenic substance into a living host, the host's immune system responds by producing antibodies to all the recognizable sites on the substance. This results in the production of antibodies of differing affinities and specificities for the immunogenic substance. Accordingly, after the different hybridoma cell lines are screened to identify those that produce antibody to the immunogenic substance, the antibodies produced by the individual hybridoma cell lines are preferably screened to identify those having the highest affinity for the immunogenic substance. In the present case, once hybridoma cell lines are screened to identify those that produce antibody to PSA-ACT, the antibodies produced by the individual hybridoma cell lines are screened to identify those antibodies that exhibit specific binding for the PSA-ACT complex and which have no significant cross-reactivity with PSA, ACT or CG-ACT.

As used herein, the phrase "antibody specific for PSA-ACT" refers to the ability of an antibody or derivative to react immunologically with PSA-ACT, to the exclusion of PSA, ACT or CG-ACT.

The antibodies which specifically bind PSA-ACT may also be immunologically reactive derivatives of the antibodies. "Immunologically reactive derivative" of an antibody refers to portions of the antibody which retain the ability to recognize the epitopes ordinarily recognized by the antibody from which they are derived. Such derivatives commonly include, for example, Fab, Fab', F(ab')$_2$ fragments of immunoglobulins. Preparation of such immunologically reactive derivatives is well understood in the art.

The anti-PSA and anti-ACT antibodies used to block immunodominant antigenic sites on the PSA-ACT complex can alternatively be immunologically reactive derivatives of the antibodies. These antibody fragments can be prepared by methods known in the art (E. Ishikawa, Journal of Immunoassay, 3:209–327, 1983). One such method of preparing anti-PSA and anti-ACT antibody fragments is exemplified below.

"Cross-reactive with" in describing the characteristics of an antibody or its derivatives refers to the ability of the antibody to recognize another analyte or epitope in addition to the target analyte or epitope. In a preferred embodiment, the anti-PSA-ACT antibodies of the present invention are less than 20% cross-reactive with PSA, ACT or CG-ACT. In specific embodiments of the present invention, antibodies against PSA-ACT are less than 1%, and most preferably less than about 0.1% cross-reactive with PSA; less than 10%, and preferably less than about 6% cross-reactive with ACT; and less than 15%, and preferably less than about 12% cross-reactive with CG-ACT.

"Cell line" refers to an immortalized cell, cell culture, multiplicity of identical cells, and the progeny thereof. It is recognized that the progeny, and some of the members of the "identical" collection may not be absolutely identical to the original cell from which the line is derived, but may differ in genetic makeup due to chance mutations. These mutated progeny are, however, included within the definition as long as the essential characteristics of the cell line are maintained. In terms of the present invention, a cell or its progeny falls within the definition so long as the ability to secrete antibodies of the required characteristics, i.e., specificity for the PSA-ACT complex, is retained.

A preferred embodiment of the present invention is an immunoassay to detect PSA-ACT in a sample. The immunoassay comprises at least one monoclonal antibody that preferentially binds PSA-ACT. The immunoassay may comprise two monoclonal antibodies. In this embodiment, the first monoclonal antibody may be an anti-PSA-ACT monoclonal antibody and the second monoclonal antibody may be an anti-PSA monoclonal antibody, an anti-ACT monoclonal antibody, or another anti-PSA-ACT monoclonal antibody. In a preferred embodiment, the second monoclonal antibody is an anti-PSA monoclonal antibody. One or more of the monoclonal antibodies may be labeled. A preferred assay comprises an enzymatically labeled monoclonal antibody.

The immunoassay of the present invention may also utilize a monoclonal antibody which is immobilized on a solid support. The solid support may be composed, for example, of materials such as glass, paper, polystyrene, polypropylene, polyethylene, dextran, nylon, amylases, natural and modified celluloses, polyacrylamides, agaroses, or magnetite. The nature of the support can be either soluble to some extent or insoluble for the purpose of the present invention. The support material may have virtually any possible structural configuration. Thus, the support configuration may be spherical, as in a bead, or cylindrical, as in the inside surface of a test tube, or the external surface of a rod. Alternatively, the surface may be flat, such as a sheet, test strip, etc. Those skilled in the art will note many other suitable carriers for binding monoclonal antibody, or will be able to ascertain the same by use of routine experimentation, In one embodiment, the support will be a polystyrene microtiter plate.

Numerous immunoassay formats and procedures are known in the art. Conventional radioimmunoassay (RIA) procedures, for example, were described by Yalow et al., J. Clin. Invest., 39:1157, 1960. The immunoassay of the present invention can be in any format, although a preferred immunoassay utilizes an enzymatic microtiter plate (MP) immunoassay format.

The immunoassay may be enhanced by several means, including the addition of detergent, for example, NP-40, to the assay incubation buffer. Addition of NP-40 to the immunoassay has been found to beneficially reduce the non-specific binding, especially of ACT and its complexes in serum. The amount of NP-40 added to the immunoassay is sufficient to reduce the non-specific binding, with a preferred embodiment using a concentration of NP-40 of about 0.4%.

Non-specific binding can also be reduced by the addition of microparticles to the immunoassay. The microparticles are preferably made of latex. Any size microparticles may be used which reduce the non-specific binding, however, most preferably, latex microparticles of approximately 0.088 micron are used. The concentration of microparticles is sufficient to beneficially reduce non-specific binding. In a preferred embodiment, a concentration of latex microparticles of approximately 0.1% is used.

The invention is further embodied by the following non-limiting examples.

EXAMPLE 1

Formation and Purification of PSA-ACT Complex

The PSA-ACT complex was prepared using a 2:1 molar ratio of ACT to PSA, in the following manner. Four mg ACT (L/N AX9407, 1 mg in 308 μl of 20 mM Tris, pH 7.4 in 200 mM NaCl; Athens Research and Technology) and 1 mg of purified PSA (L/N 8077:24, at 0.969 mg/ml) were added to a test tube. 1.7 ml of Tris 50 mM buffer was added for a total volume of 4 ml and mixed well. The mixture was incubated at 37 degrees C. for three to five hours at pH of 8.

The solution was made 1.2M ammonium sulfate by the addition of solid ammonium sulfate. The sample was applied to a hydrophobic interaction chromatography (HIC) column (polypropyl aspartamide, PolyLC) which was developed in a gradient from 0–35% buffer (50 mM sodium phosphate, 5% v/v 2-propanol, pH 7.3) in 1 minute, 35–60% buffer in 10 minutes.

Under these conditions, PSA-ACT eluted at about 9 minutes and unreacted PSA eluted at about 12 minutes. The PSA-ACT peak was collected and exchanged into a suitable buffer, for example, PBS, by repeated concentration with 30K ultrafiltration membrane An absorbance of 1.0 at 280 nm was equal to 1 mg/ml complex

EXAMPLE 2

Formation of Anti-PSA and Anti-ACT Blocking Antibodies

Specific monoclonal antibodies against PSA and ACT were obtained. Four anti-PSA antibodies and two anti-ACT antibodies were generated and used as blocking antibodies to inactivate dominant antigenic sites on the PSA-ACT complex. Each blocking antibody appeared to be specific to a particular epitope on the PSA or ACT molecule. Four anti-PSA clones and two anti-ACT clones were generated by fusing either Balb/c or A/J spleen cells with P3.653 or SP2/0 myeloma cells.

PSA 399.4, an IgG 2b monoclonal antibody producing cell line, was generated by fusing SP2/0 myeloma cells with Balb/c spleen B cells and then subcloned using a limiting dilution method. Balb/c mice were immunized four times intraperitoneally (IP) with 10 μg purified PSA with alum adjuvant. Three days after an additional intravenous (IV) boost with antigen (10 μg) in saline, the mice were sacrificed for fusion. PSA 399 and its subclone 399.4 were selected based on the reactivity to PSA by radioimmunoassay (RIA). Also selected from this fusion, were the IgG 1 antibodies PSA 795 and PSA 187.

PSJ 206, an IgG 1 monoclonal antibody producing cell line, was generated by fusing P3.653 myeloma cells with Balb/c spleen B cells. Balb/c mice were immunized three times intraperitoneally with 10 μg PSA with alum adjuvant. Three days after an additional boost with antigen (10 μg) in saline, the mice were sacrificed for fusion. PSJ 206 was selected based on the reactivity to PSA by RIA.

PSM 80, an IgG 1 monoclonal antibody producing cell line, was generated by fusing SP2/0 myeloma cells with Balb/c spleen B cells. Balb/c mice were immunized twice intraperitoneally with 5 μg PSA with alum adjuvant. Three days after an additional boost with antigen (10 μg) in saline, the mice were sacrificed for fusion. Included in the final boost was 100 μg of anti-PSA antibody, PSA 795, which appeared to block a common epitope and resulted in obtaining an epitope-specific anti-PSA antibody. PSM 80 was selected based on the reactivity to PSA by RIA.

PSM 773.3, an IgG 1 monoclonal antibody producing cell line, was generated by fusing SP2/0 myeloma cells with Balb/c spleen B cells and then subcloned using a limiting dilution method. Balb/c mice were immunized twice intraperitoneally with 5 μg purified PSA with alum adjuvant. Three days after an additional intravenous boost with antigen (10 μg) in saline, the mice were sacrificed for fusion. Included in the final boost was 100 μg of anti-PSA antibody, PSA 187, which resulted in an antibody that appeared to be specific to a particular epitopic site on PSA. PSM 773 and its subclone 773.3 were selected based on the reactivity to PSA by RIA.

AC1A 212, an IgG 1 monoclonal antibody producing cell line, was generated by fusing P3.653 myeloma cells with Balb/c spleen cells. Balb/c mice were immunized three times intraperitoneally with 50 μg of ACT. Complete and Incomplete Freund's adjuvants (Difco, Detroit, Mich.) were applied in the first and the second injections, respectively. Three days after an additional intravenous boost with antigen (50 μg) in saline, the mice were sacrificed for fusion. AC1A 212 was selected based on the reactivity to ACT by RIA.

AC1A 285, an IgG 1 monoclonal antibody producing cell line, was generated by fusing P3.653 myeloma cells with A/J spleen cells. Balb/c mice were immunized three times intraperitoneally with 50 μg of ACT. Complete and Incomplete Freund's adjuvants were applied in the first and second injections, respectively. Three days after an additional intravenous boost with antigen (50 μg) in saline, the mice were sacrificed for fusion. AC1A 285 was selected based on the reactivity to ACT by RIA.

The following two tables summarize the procedures used to obtain the anti-PSA and anti-ACT monoclonal antibodies.

TABLE 1

Anti-PSA Antibodies

| Clone Name | Parent | Immunization | Isotype |
|---|---|---|---|
| PSA 399.4 | Balb/c × SP2/0 | 4x, 10 μg PSA, alum, IP FB: 10 μg PSA, PBS, IV | IgG 2b |

TABLE 1-continued

Anti-PSA Antibodies

| Clone Name | Parent | Immunization | Isotype |
|---|---|---|---|
| PSJ 206 | Balb/c × P3.653 | 3x, 10 μg PSA, alum, IP FB: 10 μg PSA, IV | IgG 1 |
| PSM 80 | Balb/c × SP2/0 | 2x, 5 μg PSA, alum, IP FB: 10 μg PSA + 100 μg PSA 795, IV | IgG 1 |
| PSM 773.3 | Balb/c × SP2/0 | 2x, 5 μg PSA, alum, IP FB: 10 μg PSA + 100 μg PSA 187, IV | IgG 1 |

TABLE 2

Anti-ACT Antibodies

| Clone Name | Parent | Immunization | Isotype |
|---|---|---|---|
| AC1A 212 | Balb/c × P3.653 | 3x, 50 μg ACT, (CFA/IFA/PBS), IP FB: 50 μg ACT, IV | IgG 1 |
| AC1A 285 | A/J × P3.653 | 3x, 50 μg ACT, (CFA/IFA/PBS), IP FB: 50 μg ACT, IV | IgG 1 |

EXAMPLE 3

Generation of Blocking Antibody Fab Fragments

Fabs of monoclonal antibodies specific for PSA and ACT were prepared with an ImmunoPure® Fab preparation kit (Pierce). The antibodies were concentrated to about 10 mg/ml and dialyzed against 20 mM phosphate containing 10 mM EDTA, pH 7.0.

The digestion buffer was prepared by dissolving 42 mg cysteine.HCl in 12 ml of the supplied Phosphate Buffer, pH 7.0±0.2.

The immobilized papain was equilibrated with the digestion buffer. Four mls of the digestion buffer were added to the immobilized papain, separated with the separator tube, and this procedure repeated with an additional 4 mls of buffer. The immobilized papain was then resuspended in 0.5 ml of digestion buffer.

One ml of antibody was added to the tube containing the immobilized papain. The mixture was incubated for 5 hours in a shaker at 37° C. at high speed. The solubilized Fab and Fc fragments and undigested IgG were recovered from the immobilized papain with the separator tube. The crude digest was decanted into a clean tube. The immobilized papain was washed with 1.5 ml of Immunopure IgG binding buffer with the wash and crude combined to give 3.0 ml sample.

A column was equilibrated with 13 ml of binding buffer. 3.0 mls of the crude digest were added to the column and allowed to completely flow into the gel. The column was washed with 6.0 mls of Immunopure Binding Buffer. The eluate (flow through material) which contained the Fab fragments was collected. The Fabs were dialyzed against phosphate buffered saline.

EXAMPLE 4
Immunogen Preparation

The immunogen was prepared by reacting PSA-ACT complex with the Fab fragments of the blocking monoclonal antibodies against PSA and ACT. Four anti-PSA Fabs, PSJ 206, PSM 773, PSM 80 and PSA 399.4, and two anti-ACT Fabs, AC1A 212 and AC1A 285, were used. The immunogen was prepared by reacting 2 molar excess of the Fab fragments with PSA-ACT complex at 4° C., for a minimum of 24 hours. The desired product immunogen was separated from the reactants by size exclusion high pressure liquid chromatography (SEC-HPLC). Two Biorad Biosil SEC 250 gel filtration HPLC columns in tandem were run at 0.5 ml/min equilibrated with PBS buffer (Boehringer Mannheim). The absorbance at 280 nm of each fraction was determined and the high molecular weight peak was pooled. The sized complex was concentrated with an Amicon® Centricon-3 concentrator.

EXAMPLE 5
Immunizations

Immunogen prepared in accordance with Example 4 was used to immunize six female Balb/c mice (9 weeks old). The immunogen was separately prepared prior to each immunization. Mice were immunized by intraperitoneal injection. The first injection was with 50 µg immunogen emulsified 1:2 in Complete Freund's adjuvant. The first injection was followed two weeks later with a second injection of 25 µg immunogen emulsified 1:2 in Incomplete Freund's adjuvant. This was followed two weeks later with a third injection with 25 µg immunogen in PBS.

One week after the third injection the mice were bled and a serum titer assay was performed

EXAMPLE 6
Serum Titer Assay

Serum from mice that were immunized with immunogen was tested for reactivity to PSA-ACT. The purpose of the assay was to screen the sera for anti-PSA-ACT antibodies.

Avidin coated microplates were used to capture biotin labeled PSA-ACT. Avidin coated microplates were blocked with 200 µl/well of the blocking buffer (phosphate buffer containing 2% BSA and 0.2% Tween 20) for one hour at room temperature. The protein and detergent in this buffer coats the plate to minimize non-specific binding in the assay.

The plates were then washed. The wash procedure was the same throughout. The plates were filled with approximately 300 µl of phosphate buffer containing 0.1% Tween 20 and then emptied. This was repeated twice. The plate was then washed three times by filling the wells with distilled water and emptying them. The plates were then dried.

PSA-ACT was biotinylated in advance. 100 µg PSA-ACT was diluted 1:10 in 0.5 sodium bicarbonate buffer, pH 8.5. A 7 molar excess of Pierce #21335 Immunopure NHS-LC-Biotin in DMSO was added and incubated for 2 hours on ice. The PSA-ACT was then dialyzed overnight against 100 fold excess PBS changed at least two times.

The test sera and biotinylated PSA-ACT were then added to the wells. Fifty microliters of biotinylated PSA-ACT (100 ng/ml in phosphate buffer containing 2% BSA and 0.2% Tween 20) and fifty microliters of the test serum were added to each well and allowed to incubate one hour at room temperature in a platform shaker (Lab Line Instruments) at a speed setting of 7.

The plates were washed as above.

An anti-mouse horse radish peroxidase labeled conjugate was added which bound to the mouse antibody. Fifty microliters of goat anti-mouse horse radish peroxidase (HRP) conjugate specific for mouse Fc (conjugate) diluted in HH4 media containing 10% horse serum was added to each well. The plate was again incubated for one hour at room temperature on the platform shaker.

The plates were again washed as above.

A calorimetric substrate (OPD) was added which turned into a colored product in the presence of horse radish peroxidase. One hundred microliters of the OPD substrate were added per well and allowed to incubate for thirty minutes at room temperature on the platform shaker. After the 30 minute incubation, one hundred microliters of 4N sulfuric acid were added to each well. The plates were then read at 490 and 540 nm and the data recorded.

Serum titers were performed on 6 PSA-ACT immunized mice. Two Balb/c mice with the highest serum titers to PSA-ACT were selected for fusion PX1G. The selected mice were injected with 10 µg PSA-ACT, intravenously, three days prior to fusion.

EXAMPLE 7
PX1G Fusion

On the day of fusion, the spleens of the selected mice were removed sterilely and placed in petri dish with PBS. The spleens were teased apart with two 23G needles attached to 1 ml syringes. Cells were transferred to a sterile 15 ml conical tube and clumps allowed to settle. Cells were then counted.

Fusion was done using a Tcell depletion protocol.
Tcell Depletion

Red blood cells in the spleen cell suspension were lysed with 0.84% ammonium chloride for fifteen minutes at 4° C. This was followed by underlaying cells with horse serum and centrifuging to remove dead cells. Spleen cells were then incubated with anti-Thy 1.2 which binds to T lymphocytes for forty five minutes at 4° C. This was followed by a incubation step with rabbit complement for forty five minutes at 37° C. to lyse the T lymphocytes. Cells were then counted and prepared for fusion. Fusion Spleen cells were co-pelleted with P3.653 myeloma cells in a ratio of 1:4 by centrifuging. Fusion of spleen cells and myeloma cells was done by sequential additions of polyethylene glycol, serum free media, and fusion media (HH4 media and 10% fetal bovine serum and HAT). Cells were resuspended to $1\times10^6$ cells/ml and plated at 200 µl/well in 96 well plates.

The plates were incubated at 37° C. and 5% $CO_2$ and fed on day 5 with 150 µl HH4, 10% FBS and HAT. The plates were fed two times per week until greater than fifty percent of the colonies were confluent. At that time, culture supernatant was harvested and an initial screen was done against PSA-ACT. After the initial screen, positive hybridomas with a differential between PSA-ACT and either ACT or PSA were expanded to 2 ml cultures in 24 well plates. When cells were confluent, the culture supernatants were titered again. Cells were expanded further and 4 wells of the 24 well plate were pooled and frozen. Hybridomas to be kept were subcloned using a FACStar Plus equipped with an Automatic Cell Deposition Unit.

EXAMPLE 8
Fusion Screening

To obtain monoclonal antibodies which reacted to PSA-ACT, but had minimal reactivity to either PSA or ACT, the differential reactivity of the antibodies was evaluated by screening each hybridoma supernatant against PSA-ACT, PSA and ACT. The results were normalized to the positive control and the differential reactivity was evaluated. The differential reactivity to PSA, for example, was calculated by taking the reactivity to PSA-ACT over PSA. This reactivity ranged from 1 where the antibody reacted equally well with PSA-ACT and PSA to 20 fold or more where there was no reactivity to PSA. The differential reactivity to ACT was evaluated in a similar manner. The following table summarizes the differential reactivity of the monoclonal antibodies obtained.

TABLE 3

Differential Reactivity of Anti-PSA-ACT Antibodies

| Hybrid Number | PSA-ACT | PSA | ACT | PSA-ACT:ACT | CG-ACT | PSA-ACT:CG-ACT |
|---|---|---|---|---|---|---|
| 54 | 3.1 | 0.054 | 0.64 | 5 | 1.05 | 3 |
| 283 | 4 | 0.06 | 1.1 | 4 | 1.58 | 3 |
| 359 | 3.7 | 0.08 | 0.85 | 4 | 1.35 | 3 |
| 460 | 4.1 | 0.09 | 0.75 | 5 | 1.35 | 3 |
| AC1A 212 | 6.7 | 0.007 | 6.4 | 1 | 5.6 | 1 |

The hybridomas represented by hybrid Numbers 54, 283, 359, and 460 are respectively mouse hybridomas PX1 G054, PX1G283, PX1G 359, and PX1G460. The preferred hybridomas were deposited on Mar. 26, 1997 with the American Type Culture Collection (ATCC), 10801 University Boulevard, Manasssas, Va. 20110-2209, USA, given accession numbers as shown: ATCC HB-12328 for mouse hybridoma PX1G054, ATCC HB-12326 for mouse hybridoma PX1G283, ATCC HB-12325 for mouse hybridoma PX1G359, and ATCC HB-12327 for mouse hybridoma PX1G460.

This data was obtained with the same protocol used with the serum titers in the example above. Biotinylation of PSA-ACT and ACT was performed in the same manner as PSA in the earlier example. The primary screen was against PSA-ACT. Antibodies that reacted against PSA-ACT were retained. The secondary screen was against PSA-ACT, PSA, ACT and CG-ACT. Antibodies that showed potential differential reactivity for PSA-ACT were retained.

EXAMPLE 9

PSA-ACT Immunoassays

Immunoassays were developed using the antibodies obtained in accordance with embodiments of the present invention. The immunoassays utilized an enzymatic microtiter plate format and included at least one anti-PSA-ACT antibody as described herein. The immunoassays were used to demonstrate the clinical utility of the PSA-ACT assay.

Calibrator and sample volumes were added to streptavid-incoated wells of a 96 well microtiter plate (50 μl per well). The calibrators comprised solutions of a protein-containing buffer (10% BSA, pH 8) and known concentrations of PSA-ACT, ranging from about 0 to 20 ng/ml. The samples to be tested contained unknown concentrations of PSA-ACT. Fifty μl of biotinylated capture antibody (PSA 399) were then added to each well. One hundred μl of diluent (buffer solution containing BSA) were then added to each well to maintain a high reaction volume. Also added to the diluent was approximately 0.4% NP-40 detergent and approximately 0.1% latex microparticles having a diameter of approximately 0.088 microns. The plate was shaken for 1 hour at room temperature and washed with Tandem® Wash Solution (Hybritech Incorporated, San Diego, Calif.).

Next 100 μl of conjugate were added to the wells. The conjugate comprised a solution of alkaline phosphatase covalently linked to anti-PSA-ACT antibody. The plate was again shaken for 2 hours at room temperature and washed with buffer solution.

One hundred μl of substrate were then added to the microtiter plate wells. The substrate was a solution of para-nitrophenylphosphate (PNPP), available in the Tandem® PSA-MP assay, also from Hybritech Incorporated, San Diego, Calif. The plate was then shaken for 30 minutes at room temperature. One hundred μl of Tandem® Quench Solution (solution of EDTA) was then added. The absorbance of each of the wells was measured at 450 nm and correlated to the concentration of PSA-ACT in the sample.

Forty four benign prostatic hyperplasia (BPH) and 39 prostate cancer specimens were tested in various assays and the sensitivity and specificity of the assays were calculated. It was determined that the optimal curve was obtained when the ratio of the complexed PSA assay value to the total PSA value was made (c/t). FIG. 3 shows the receiver operating characteristic (ROC) plot for the complex/total PSA assay values using PX1G 359 as the anti-PSA-ACT antibody and this is compared to the total PSA assay values (tPSA). FIG. 4 is the same ROC plot for the PX1G 460 assay.

The invention is not limited to the exact details shown and described, for it should be understood that many variations and modifications may be made while remaining within the spirit and scope of the invention as defined by the following claims.

What is claimed is:

1. A monoclonal antibody or fragment thereof which specifically binds the complex of prostate specific antigen (PSA) and protease inhibitor $\alpha_1$-antichymotrypsin (ACT) and which does not significantly cross-react with PSA, ACT or cathepsin G-ACT (CG-ACT).

2. A monoclonal antibody or a fragment thereof which specifically binds the complex of prostate specific antigen (PSA) and protease inhibitor $\alpha_1$-antichymotrypsin (ACT) and which does not significantly cross-react with PSA, ACT or cathepsin G-ACT (CG-ACT), wherein the monoclonal antibody is selected from the group consisting of PX1G 54, PX1G 283, PX1G 359 and PX1G 460.

3. A hybridoma cell line capable of producing a monoclonal antibody which specifically binds a PSA-ACT complex and which does not significantly cross-react with PSA, ACT or CG-ACT.

4. A hybridoma cell line capable of producing a monoclonal antibody which specifically binds a PSA-ACT complex and which does not significantly cross-react with PSA, ACT or CG-ACT, wherein the hybridoma cell line is capable of producing a monoclonal antibody selected from the group consisting of PX1G 54, PX1G 283, PX1G 359 and PX1G 460.

* * * * *